US00PP33705P2

(12) United States Plant Patent
Van Swieten

(10) Patent No.: US PP33,705 P2
(45) Date of Patent: Nov. 30, 2021

(54) ***PHALAENOPSIS* ORCHID PLANT NAMED 'PHALILWI'**

(50) Latin Name: ***Phalaenopsis* hybrid**
Varietal Denomination: PHALILWI

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/300,387

(22) Filed: Jun. 10, 2021

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02
See application file for complete search history.

*Primary Examiner* — Kent L Bell
(74) *Attorney, Agent, or Firm* — Jondle & Associates, P.C.

(57) ABSTRACT

A new and distinct variety of *Phalaenopsis* plant named 'PHALILWI', particularly characterized by very light purple, flecked flowers with reddish-purple lips, a convex flower shape in lateral view, an apical lobe of the lip that is dotted and striped, and is propagated by meristem tissue culture, is disclosed.

3 Drawing Sheets

Genus and species: *Phalaenopsis* hybrid.
Variety denomination: 'PHALILWI'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALILWI'.

The new *Phalaenopsis* plant is a product of a planned breeding program conducted by the inventor in Bleiswijk, the Netherlands. The objective of this breeding program was to create a new *Phalaenopsis* plant with very light purple, flecked flowers with reddish-purple lips, suitable for potted plant production.

The new *Phalaenopsis* plant 'PHALILWI' is a result of cross-pollination made by the inventor in March 2008 in Bleiswijk, the Netherlands, of the proprietary female, or seed parent, *Phalaenopsis* hybrid '6240-02' (unpatented) with the proprietary male, or pollen parent, *Phalaenopsis* hybrid '01-1806' (unpatented).

The new *Phalaenopsis* was selected by the inventor as a single plant within the progeny of the stated cross-pollination in a controlled greenhouse in Bleiswijk, the Netherlands, in February 2015. Asexual reproduction of the new *Phalaenopsis* plant by meristem tissue culture since 2016 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 20, 2019 (Application no. 2019/2315), by Applicant who obtained the subject matter disclosed directly from the inventor. 'PHALILWI' has not been made publicly available or sold anywhere in the world prior to the effective filing date of this application with the exception of sales or disclosures made one year or less before the effective filing date of this claimed invention by Applicant who obtained 'PHALILWI' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALILWI' as a new and distinct variety of *Phalaenopsis* plant:

1) Very light purple, flecked flowers with reddish-purple lips (the intensity and number of flecks depend on temperature);
2) Flower shape in lateral view is convex; and
3) Apical lobe of the lip is dotted and striped.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in February 2021. Colors in the photographs may differ from the color values cited in the detailed botanical description, which accurately describe the actual colors of the new variety.

DESCRIPTION OF THE NEW VARIETY

Figure 1:
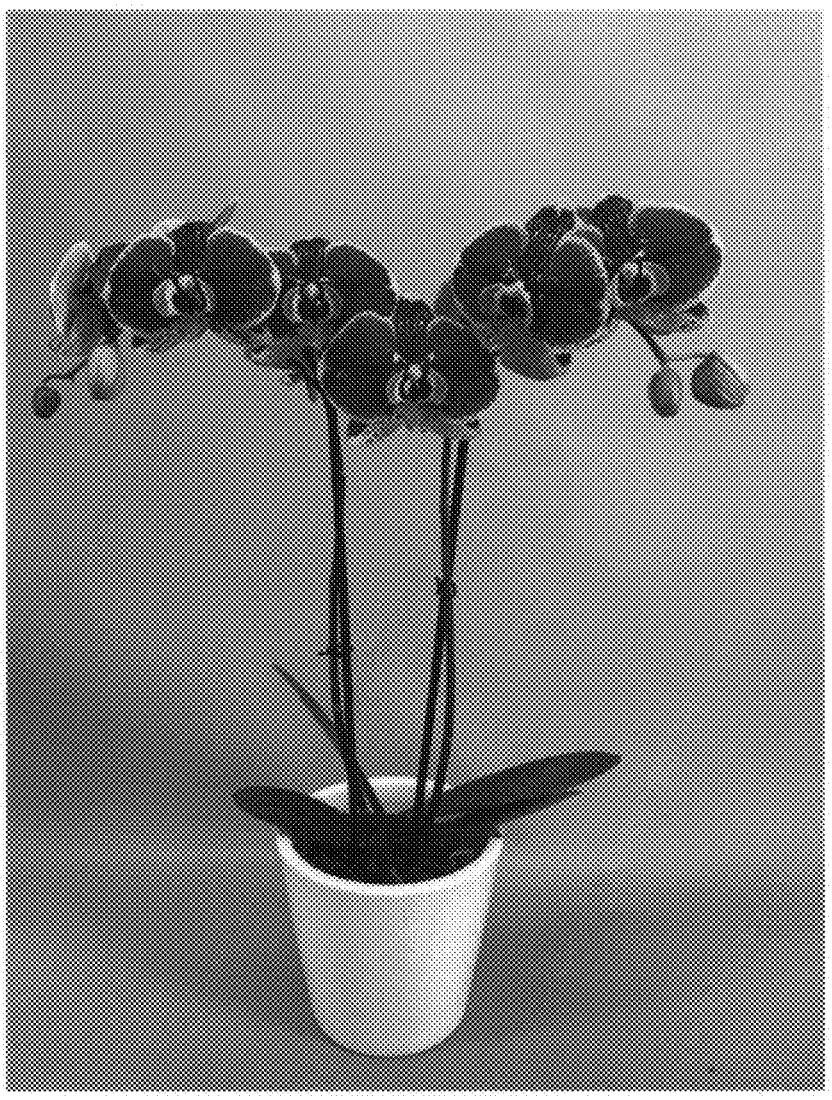
FIG. 1 shows the overall plant habit, including blooms, buds, and foliage of 'PHALILWI'.
Figure 2:
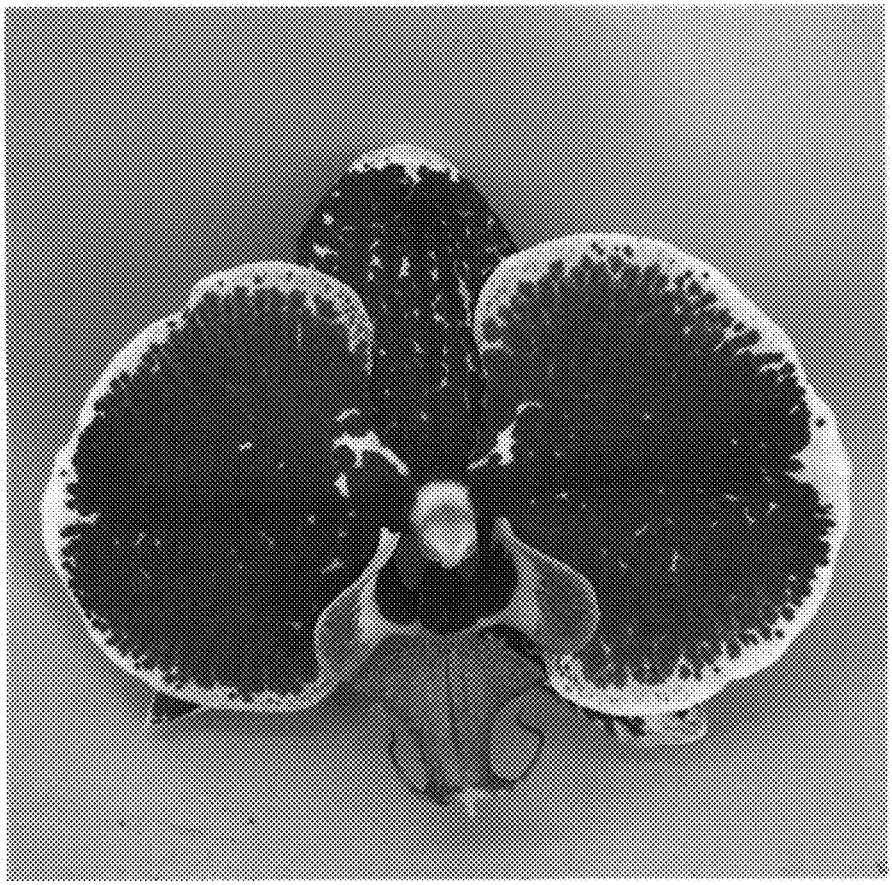
FIG. 2 shows a close-up of a flower of 'PHALILWI'.
Figure 3:
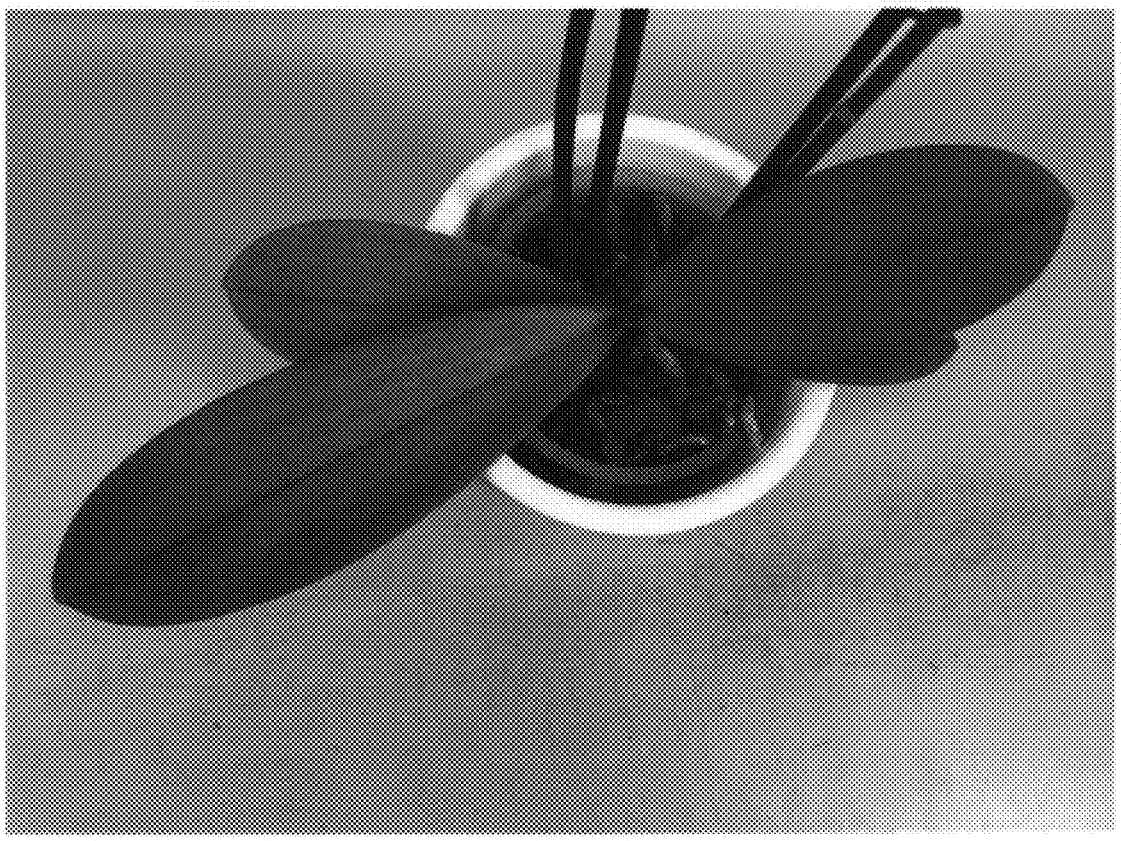
FIG. 3 shows an overhead view of the leaves of 'PHALILWI'.

The following detailed description sets forth the distinctive characteristics of 'PHALILWI'. Plants of the new

*Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in February 2021 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALILWI'.

Parentage:

*Female parent*.—*Phalaenopsis* cultivar '6240-02' (unpatented).

*Male parent*.—*Phalaenopsis* cultivar '01-1806' (unpatented).

Propagation:

*Type*.—Meristem tissue culture.

Roots:

*Root description*.—Greyed-green (a color in between RHS 190B and RHS 190C) colored roots with branching lateral roots having yellow-green (RHS 145C) with a hint of purplish-red (RHS N77B) and dark purplish-red (RHS N79C) colored root tips.

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with raceme inflorescence.

*Height* (*from soil level to top of inflorescence*).—Approximately 45.0 cm to 50.0 cm.

*Width* (*measured from leaf tips*).—About 31.0 cm to 33.0 cm.

*Vigor*.—Strong.

Leaves:

*Mature leaves*.—Quantity per plant: 5 to 7 leaves are produced before flowering. Length (fully expanded): 16.0 cm to 19.0 cm. Width: 5.5 cm to 6.5 cm. Position of the broadest part of the leaf: At the middle. Shape: Obovate. Base shape: Moderately elongated. Apex: Obtuse unequal. Leaf blade angle with the petiole (measured from the horizontal position): Between 20 degrees and 40 degrees. Leaf margin: Entire. Color: Upper surface: RHS 146B with a brown margin (RHS 200C). Lower surface: RHS 146C with reddish-brown margin (a color in between RHS 200B and RHS 187A). Texture (both upper and lower surfaces): Smooth. Thickness: 2.0 mm to 3.0 mm. Variegation: Absent. Venation: Pattern: Parallel. Color of the midvein: Upper surface: RHS 146B. Lower surface: A color in between RHS 200B and RHS 187A.

Peduncle:

*Quantity per plant*.—1 to 2.

*Number of flowers per peduncle*.—7 to 9.

*Length*.—45.0 cm to 50.0 cm.

*Diameter*.—5.0 mm to 6.0 mm.

*Strength*.—Strong.

*Aspect*.—Upright to slightly pendent.

*Texture*.—Smooth.

*Color*.—Reddish-brown (a color in between RHS 200B and RHS 187A) with a touch of yellow-green (RHS 146D).

*Internode length*.—5.5 cm to 6.5 cm.

Inflorescence description:

*Appearance*.—Upright to slightly pendent, raceme inflorescence with bilaterally symmetrical flowers that open in succession beginning with the lowermost flower.

*Number of inflorescences*.—1 to 2.

*Inflorescence size*.—Height (from base to tip): 180.0 mm to 200.0 mm.

*Flowering time*.—First flowers can be expected 10 to 11 months after planting in a 12-cm pot.

*Flower*.—Height: 75.0 mm to 80.0 mm. Diameter: 90.0 mm to 95.0 mm. Depth of lip: 26.0 mm to 28.0 mm.

*Flower longevity*.—On the plant: 9 to 11 weeks.

*Flower shape*.—Convex.

*Fragrance*.—Absent.

*Flower bud*.—Average size: Medium to large. Length: 23.0 mm to 25.0 mm. Width: 18.0 mm to 20.0 mm. Shape: Egg shaped. Color: Yellow-green (RHS 146D); dark purplish-red (RHS N79C and RHS N79B) toward the tip.

*Petals*.—Arrangement: Open/free. Shape: Semi-circular. Apex: Rounded to slightly emarginated asymmetric. Margin: Moderately undulated. Length (from base to tip): 40.0 mm to 42.0 mm. Width: 53.0 mm to 55.0 mm. Position of the broadest part of the petal: Toward the base. Color (when fully opened): Upper surface: Basic color: Very light purple (RHS 76C). Over color: Dark reddish-purple flecks (a color in between RHS 187B and RHS N79C). Lower surface: Basic color: Very light purple (RHS 76B). Over color: Light reddish-purple shade (RHS N78D); diluting flecks (a color in between RHS N77A and RHS N77B). Number of spots, flecks, and stripes on the petals (upper surface): Very many flecks. Color of spots, flecks, and stripes on the petals (upper surface): A color in between RHS 187B and RHS N79C. Density of netting of the petals (upper surface): None. Color of the netting (upper surface): Not applicable.

*Dorsal sepal*.—Shape: Elliptic. Apex: Obtuse symmetric. Margin: Moderately undulated. Length (from base to tip): 44.0 mm to 46.0 mm. Width: 27.0 mm to 29.0 mm. Position of the broadest part of the dorsal sepal: At the middle. Color (when fully opened): Upper surface: Basic color: Light purple (a color in between RHS 76A and RHS 76B). Over color: Dark reddish-purple flecks (a color in between RHS 187B and RHS N79C). Lower surface: Basic color: Light reddish-purple (a color in between RHS 76A and RHS N78D). Over color: Yellow-green (RHS 195B); purplish-pink vein (RHS N78C) and diluting flecks (a color in between RHS N77A and RHS N77B). Number of spots, flecks, and stripes on the dorsal sepals (upper surface): Many flecks. Color of spots, flecks, and stripes on the dorsal sepals (upper surface): A color in between RHS 187B and RHS N79C. Density of netting of the dorsal sepals (upper surface): None. Color of the netting: Not applicable.

*Lateral sepals*.—Shape: Ovate. Apex: Obtuse symmetric. Margin: Moderately undulated. Length (from base to tip): 44.0 mm to 46.0 mm. Width: 26.0 mm to 28.0 mm. Position of the broadest part of the lateral sepals: At the base. Color (when fully opened): Upper surface: Basic color: Very light purple (RHS 76D). Over color: Light yellow-green (RHS 145D) from the base; dark purplish-red flecks (a color in between RHS 187B and RHS N79C); purplish-pink shade on one side toward the tip with reddish-purple netting (RHS N78B). Lower surface: Basic color: Reddish-purple (RHS N78B). Over color: Light yellow-green (RHS 145C) at the base; reddish-purple midvein (RHS N78A); diluting flecks (a color in between RHS N77A and RHS N77B). Number of spots, flecks, and stripes on the lateral sepals (upper surface): Many flecks. Color of spots, flecks, and stripes on the lateral sepals (upper surface): A color in between RHS 187B and RHS N79C. Density of netting of the lateral sepals (upper surface): Low. Color of the netting (upper surface): RHS N78B.

*Labellum* (*lip*).—Whiskers: Present. Length of whiskers: 16.0 mm to 18.0 mm. Color of whiskers: Reddish-purple (RHS N78A) with white margins and tips (RHS NN155C). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Weakly undulated. Length: 22.0 mm to 24.0 mm. Width: 16.0 mm to 18.0 mm. Color: Upper surface: Dark red stripes (a color in between RHS 187A and RHS 187B) at the base; yellow (RHS 9A) at the base toward margin on one side; reddish-purple stripes (RHS N78A) on one side toward the tip. Lower surface: White (RHS NN155C); yellow (RHS 9B) on one side; very light purple (RHS 76B) on one side toward the tip with a touch of dark red (RHS 187C). Number of spots and stripes on the lateral lobe: Medium to many stripes. Color of spots and stripes on the lateral lobe: Few stripes at the base (a color in between RHS 187A and RHS 187B) and toward the tip (RHS N78A). Density of netting of the lateral lobe: None. Color of the netting: Not applicable.

*Apical lobe*.—Shape: Triangular. Margin: Entire. Length: 22.0 mm to 24.0 mm. Width: 21.0 mm to 23.0 mm. Color: Upper surface: Yellow (RHS 9A); dotted (RHS 187B) at the base and toward wings; reddish-purple (RHS N78B) toward whiskers with reddish-purple midvein; stripes (RHS N78A) toward margins and whiskers. Lower surface: Light purple (RHS 76A) at the middle from base toward whiskers; brownish-orange (RHS N167A) toward margins; striped (RHS N78A) toward margins; light reddish-purple (RHS N78D) at the middle from the base toward whiskers. Number of spots, dots, and stripes on the apical lobe: Many very small dots; few to medium stripes. Color of spots, dots, and stripes on the apical lobe: Dots (RHS 187B); stripes (RHS N78A). Density of netting of the apical lobe: None. Color of the netting: Not applicable.

*Callus*.—Average size: Medium to large. Height: 7.0 mm to 8.0 mm. Length: 6.0 mm to 7.0 mm. Width: 4.0 mm to 5.0 mm. Color: Dark red (RHS 187A); yellow edge and margins (RHS 9B) on front; white (RHS NN155A) on sides.

Reproductive organs:

*Column*.—Length: 10.0 mm to 12.0 mm. Diameter: 5.0 mm to 6.0 mm. Color: White (RHS NN155C) at the base and reddish-purple (RHS N78B) toward tip.

*Pollinia*.—Quantity: 2. Diameter: 0.8 mm to 1.0 mm. Color: Orange (RHS 25A).

*Ovary*.—Length: 12.0 mm to 14.0 mm. Diameter: 2.0 mm to 2.3 mm.

*Pedicel*.—Length: 35.0 mm to 37.0 mm. Diameter: 2.4 mm to 2.7 mm. Color: Yellow-green (RHS 146D) with diluting dark red flecks (RHS 187B); purplish-pink (RHS N78C) and light reddish-purple (RHS N78D) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALILWI' differs from the female parent plant '6240-02' (unpatented) in that 'PHALILWI' has calluses with a main color of dark red and weak curvature of the lateral lobes, whereas '6240-02' has calluses with a main color of yellow and strong curvature of the lateral lobes.

'PHALILWI' differs from the male parent plant '01-1806' (unpatented) in that 'PHALILWI' has flowers with a flecked pattern and weak curvature of the lateral lobes, whereas '01-1806' has flowers with a center and edge pattern and medium curvature of the lateral lobes.

'PHALILWI' is most similar to the commercial *Phalaenopsis* plants named 'PHALFUCAL' (U.S. Plant Pat. No. 29,946) and 'PHALFOXYQ' (U.S. Plant Pat. No. 29,134). 'PHALILWI' differs from the commercial variety 'PHALFUCAL' in that 'PHALILWI' has flowers with a flecked pattern, whereas 'PHALFUCAL' has flowers with a center and edge pattern. Additionally, 'PHALILWI' has wider petals and narrower leaves than 'PHALFUCAL'.

'PHALILWI' differs from the commercial variety 'PHALFOXYQ' in that 'PHALILWI' has flowers with a flecked pattern, whereas 'PHALFOXYQ' has flowers with a center and edge pattern. Additionally, 'PHALILWI' has narrower leaves than 'PHALFOXYQ'.

I claim:

1. A new and distinct variety of *Phalaenopsis* plant named 'PHALILWI', substantially as described and illustrated herein.

* * * * *